(12) United States Patent
Wimmer

(10) Patent No.: US 6,383,132 B1
(45) Date of Patent: May 7, 2002

(54) WATER, AIR AND SUCTION VALVES ON ENDOSCOPES

(75) Inventor: Viktor Josef Wimmer, Garching-Hochbruck (DE)

(73) Assignee: Xion GmbH, Berlin (DE)

( * ) Notice: Subject to any disclaimer, the term of this patent is extended or adjusted under 35 U.S.C. 154(b) by 0 days.

(21) Appl. No.: 09/463,257

(22) PCT Filed: May 20, 1998

(86) PCT No.: PCT/DE98/01408

§ 371 Date: Mar. 27, 2000

§ 102(e) Date: Mar. 27, 2000

(87) PCT Pub. No.: WO99/04682

PCT Pub. Date: Feb. 4, 1999

(30) Foreign Application Priority Data

Jul. 24, 1997 (DE) .......................... 197 31 965

(51) Int. Cl.[7] .................................. A61B 1/12
(52) U.S. Cl. ........................ 600/159; 600/101
(58) Field of Search ................ 600/159, 101–105; 606/46; 128/3–8, 276–278, 240

(56) References Cited

U.S. PATENT DOCUMENTS

| | | | | |
|---|---|---|---|---|
| 4,325,362 A | * | 4/1982 | Ouchi et al. | 128/4 |
| 4,402,310 A | * | 9/1983 | Kimura | 128/4 |
| 4,408,598 A | * | 10/1983 | Ueda | 128/4 |
| 4,550,716 A | * | 11/1985 | Kinoshita | 128/6 |
| 4,731,222 A | * | 3/1988 | Kralovic et al. | 422/37 |
| 4,852,551 A | * | 8/1989 | Opie et al. | 128/4 |
| 5,322,506 A | * | 6/1994 | Kullas | 604/30 |
| 5,348,555 A | | 9/1994 | Zinnanti | |

FOREIGN PATENT DOCUMENTS

WO PCTUS9402006 2/1994

\* cited by examiner

*Primary Examiner*—Michael Peffley
*Assistant Examiner*—Peter J Vrettakos
(74) *Attorney, Agent, or Firm*—Shaffer & Culbertson, LLP

(57) ABSTRACT

The subject matter of this invention concerns an endoscope, in particular a flexible endoscope, with a minimum of one valve which is positioned at the proximal end of an endoscope housing and which comprises a valve piston and a valve cylinder with a plurality of valve openings, with the minimum of one valve provided being designed as a valve module which is detachably connected to a complementary recess in the endoscope housing.

9 Claims, 2 Drawing Sheets

WATER, AIR AND SUCTION VALVES ON ENDOSCOPES

TECHNICAL FIELD OF THE INVENTION

The subject matter of this invention concerns an endoscope, in particular a flexible endoscope, having a housing which houses piston and cylinder type valves.

BACKGROUND OF THE INVENTION

An air/water and aspiration endoscope generally has two valves to control channels, for example, an air channel, a water channel, and an aspiration channel, which run inside the endoscope housing from the distal to the proximal end.

Using these channels and their valves, the operating personnel, for example, a physician, can perform a great number of different tasks. For example, by activating the air and/or water valve, it is possible to rinse a soiled optical system that is attached to the distal end of the endoscope with water or a mixture of air and water. A different activation mode of the air and/or water valve, on the other hand, may be used to dilate internal organs, such as intestine, stomach, etc., for the purpose of observation or surgical interventions or to facilitate the further insertion of the endoscope.

By activating the aspiration valve, on the other hand, it is possible to aspirate soiled material, secretions, water, blood or other fluids, or air, etc., from the distal end via the aspiration channel.

For this purpose, the channels are connected on the proximal end with suitable sources, i.e., positive air pressure, a water tank, and negative air pressure or a vacuum.

In particular the aspiration channel may be prone to potential soiling that can be caused by different secretions or even small solids, such as granular material or similar substances.

To clean such conventionally used endoscopes, it is therefore possible to pull out or remove the valve pistons from the cylinders, for example, by unscrewing the collars. As a result, it is therefore easy to clean the valve pistons after removal from the cylinders while the valve cylinders inside the endoscope housing must be cleaned with brushes. Since it is difficult to gain access to the valve openings in the valve cylinders, a hygienically faultless cleaning of these openings and the channels connected thereto can be accomplished only in a relatively labor-intensive manner.

Thus, the problem that this invention seeks to solve is to make available a valve for an endoscope as well as an endoscope with valves disposed on the proximal end of the endoscope, which makes possible a hygienically faultless cleaning of the valves and the channel regions connected thereto in a way that is simple and convenient, rapid and inexpensive.

SUMMARY OF THE INVENTION

By designing a plurality of valves in the form of a valve module which is detachably connected to an appropriately complementary recess in the endoscope housing, it is not only possible to remove the valve pistons from the valve cylinder, as can be done with conventional endoscopes, but the valve cylinders as such. As a result, the entire valve block that comprises several valves or the valve module of the endoscope according to this invention can be removed or taken off by the operating personnel and, being therefore readily accessible, it can be advantageously cleaned in a hygienically faultless manner, for example, in an autoclave.

Furthermore, as a result of the fact that the recess in the endoscope is of necessity larger than a valve cylinder and thus more readily accessible, cleaning with brushes is made easier.

In addition, as a result of the improved accessibility of the valve or the valve module and of the recess in the endoscope, the design according to this invention makes it easier to carry out maintenance and repair work. For example, old valves or valves of different designs can be easily replaced or changed by the operating personnel by simply replacing the entire module with new valves or with special valves intended for a specific application.

In one particular embodiment of this invention, the valve piston of a minimum of one valve in the valve cylinder is designed so as to be removable. This increases the ease of cleaning, repairing and maintaining the device even more since the ability to remove the valve piston makes the inside of each valve readily accessible so that the inside of the valve as well as the piston can be easily and comfortably cleaned in a hygienically faultless manner, for example, in an autoclave.

In the preferred embodiment of this invention, the valves are designed as air and/or water valves and/or aspiration valves. This provides the operating personnel with the following choices:

1. To blow air from the proximal end or from a source of positive air pressure that is connected to the supply tube via the air and/or water valve into the distal end into an organ, for example, the stomach, intestine, etc., of the person to be treated. Such an inflation is often necessary to make the head of the endoscope more readily movable during the insertion or to carry out a surgical intervention at the targeted site.
2. Using a different activation mode of the air and/or water valve, the operator, by means of an injection of water or a mixture of water and air, is able to rinse instruments, such as an optical system, that are soiled at the distal end, without having to interrupt the treatment by removing the endoscope.
3. And finally, by activating the aspiration valve, it is possible to siphon off secretions, solid material, blood, water, and other fluids from the distal end for medical reasons or for medical purposes.

In the preferred embodiment of this invention, the air and/or water valve is therefore connected to the air and water channels that are located inside a supply tube as well as to the air and water channels which, inside the housing of the endoscope, run in the direction of the shaft of the endoscope. As a result of different piston positions, it is thus possible for an operator to easily control the different operation modes—0—position, air, air and water mixture, and only water.

In yet another embodiment of this invention, the valve module can be inserted by means of a guide mechanism into the recess and can there be locked into position. This makes it easier to insert and remove the valve module since as a result of the fact that the valve module is automatically centered, it is no longer necessary to pay special attention to an exact final positioning.

The guide mechanism can provide a horizontal and/or vertical feed, thus ensuring that during insertion of the valve module into the recess, all sealing points are simultaneously and uniformly pressed onto and/or into their corresponding channel inlets.

As a result of the separate development of a valve module according to this invention, it is also possible to make such a module available as a separate replacement component, as a result of which an expensive repair can be avoided since the old module can be simply exchanged for a new one.

BRIEF DESCRIPTION OF THE DRAWINGS

This invention will be explained in greater detail on the basis of a practical example as illustrated in the drawing. As can be seen.

DESCRIPTION OF THE PREFERRED EMBODIMENTS

Figure 1:
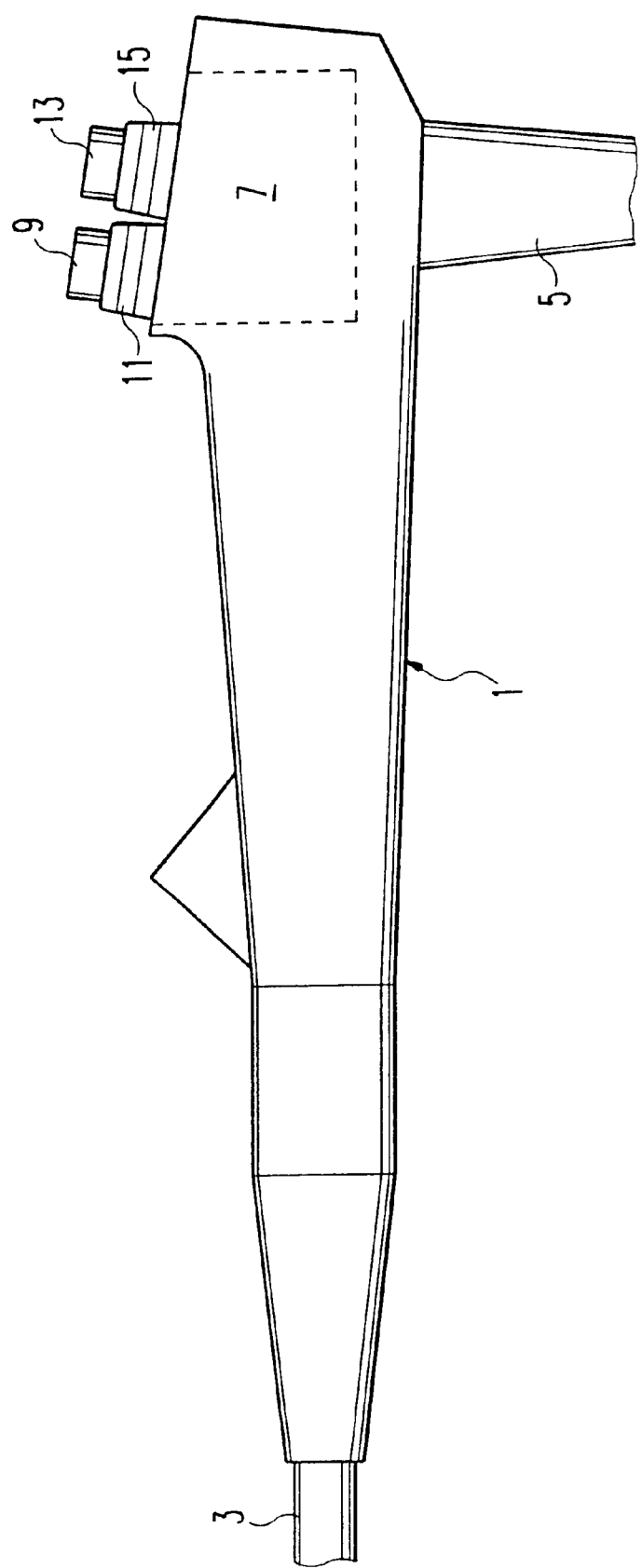
FIG. 1 shows a lateral view of an endoscope with a valve module in its inserted state and FIG. 2 shows a part-sectional exploded lateral view of an endoscope as seen in FIG. 1.

Endoscope 1 shown in FIG. 1 comprises an endoscope housing 1 and a flexible, movable endoscope guide shaft 3 connected thereto, at the distal end of which an endoscope head (not shown in the drawing) is provided. Attached to the proximal end on the lower surface of the endoscope housing is a supply tube 5 which leads to sources of positive air pressure, negative air pressure, and water (not shown in the drawing).

On the surface opposite the supply tube, the proximal end of housing 1 of the endoscope is fitted with a valve module 7 which comprises a front air and/or water valve with piston 9 and a rear aspiration valve with piston 13. As the figure shows, the upper portions of the valves extend beyond their sealing collars 11, 15 to enable manual activation. As a rule, in each of collars 11, 15, a pressure spring is provided, which serves to support the upper portion of each of valve pistons 9, 13 with respect to the stationary housing and/or collar and which activates [the pistons] by means of an upwardly directed elastic spring force.

Figure 2:
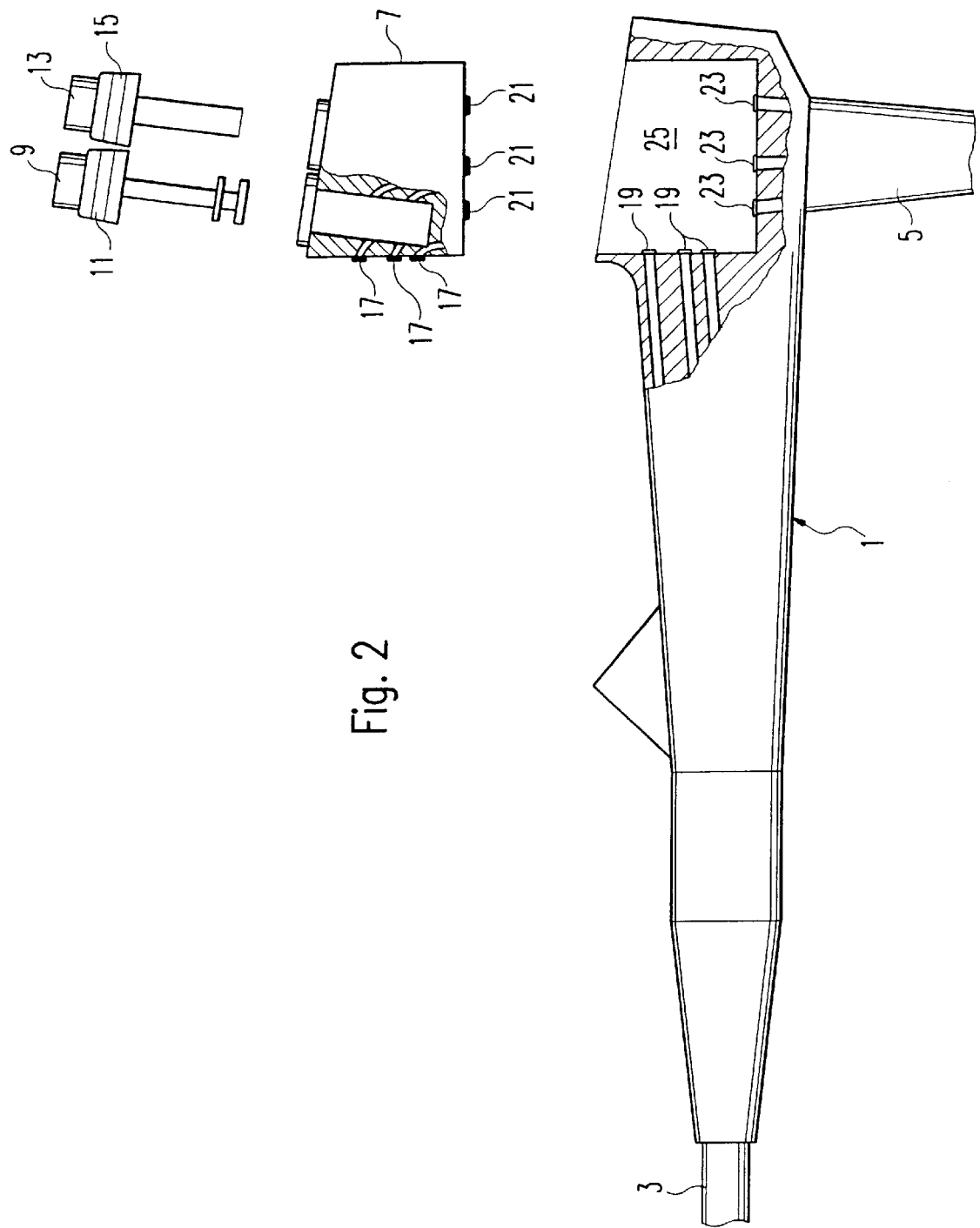

As FIG. 2 illustrates, the valve module has a cuboid shape, which is designed so as to have valve cylinders on its inside, the tops of which valve cylinders are open. Valve pistons 9, 13 can be inserted into these valve cylinders, and the lower surface of the sealing collars 11, 15 can be slipped over an upwardly fitting adapter stub with an external annular rounded protuberance, details of which are not shown in the drawing. It is obvious that any other attachment mechanisms, such as a screw cap or a catch lock, can be used to lock the valve pistons 9, 13 into position.

When inserted, module 7 is located in a complementary recess 25 at the proximal end of the endoscope housing 1. Valve module 7, the front surface of which is in contact with housing 1 when the module is inserted, has three front sealing points 17 which in the inserted position are connected in recess 25 to the channel inlets 19 that lead to shaft 3. On its lower surface, valve module 7 has three lower sealing points 21 which, when the module is inserted, are connected in recess 25 to channel inlets 23 that lead to supply tube 5. As can be only partially seen in the drawing, the lower sealing points 21 are connected to the corresponding openings in the valve cylinders via channels or conduits in the inside of the valve module. Similarly, conduits or channels in the inside of valve module 7 connect the front sealing points 17 to the corresponding openings of the valve cylinders.

When inserted in the endoscope, as shown in FIG. 1, valve module 7 connects the channels located in the supply tube and carrying positive air pressure, negative air pressure, and water (under pressure) to the channels which are located inside the housing and which run in the direction of shaft 3 up to the distal head of the endoscope. It is obvious that these channels are sealed with respect to the inside of endoscope housing 1, and the channels or conduits of valve module 7 are sealed with respect to the inside of module 7.

By activating, i.e., by pressing the aspiration valve from the outside, it is possible to open or close the openings which are generally located on the lateral surface within the cylinder, thus creating or interrupting a connection between the corresponding openings, depending on what type of operational mode is desired. As a result, when needed, a physician is able to apply a vacuum or negative air pressure present at the proximal end to a nozzle at the distal end, which enables him to siphon off fluids and/or solid material.

In the cylinder of the air and/or water valve, two supply and evacuation channels each open out, which makes it possible to use this valve to select various modes for controlling distal functions. If only the channel carrying the positive air pressure is activated, a nozzle at the distal end will generate an air jet which makes it possible, for example, to inflate an internal organ, such as the stomach, an intestine, or a similar organ. Similarly, if, on the other hand, the water channel is activated, a nozzle at the distal end will generate a water jet which, for example, can serve to rinse a potentially soiled optical system. In an in-between stage, both the air and water channel can be activated, thus generating a mixture of air and water at the distal end, which, when required, can also serve to rinse the distally located optical system.

Closing and opening the channels can be accomplished by changing the position of the appropriate valve piston 9, 13 in the longitudinal direction. Thus, valve piston 9 or 13 with protuberances that are located on its circumference, for example, in the form of O rings or similar sealing devices respectively closes or opens the openings in the valve cylinder.

Although valve module 7 as shown in the drawing has a cuboid shape, any other outside dimensions, regardless of the practical example presented here, such as concavely and/or convexly curved outer surfaces, and other outlines, such as ovals, multi-cornered shapes, etc., can be used.

But regardless of the shape of a valve module, it is useful if the outer surface of valve module 7 is fitted with guide mechanisms that interact with corresponding complementary guide mechanisms provided on the inner surface of recess 25.

Such a guide mechanism may simultaneously also provide a vertical and horizontal feed while module 7 is being inserted into recess 25. Such a slanted guide mechanism that is positioned at a certain angle between the axis of the channels in the supply tube 5 and the axis of the channels leading in the direction of shaft 3 ensures a simple and comfortable insertion of module 7 into recess 25. As a result, it is also possible to ensure that sealing points 17, 21 are simultaneously and uniformly pressed into and onto the corresponding channel inlets 19, 21.

It is useful to design sealing points 17, 21 in such a way that they comprise sealing devices, for example, sealing rings, rubber adapter stub, or similar sealing devices, which, when inserted, interact with the potentially concentrically expanding channel inlets 19, 23. In this case, the parts of the sealing connection that are subject to wear, i.e., the sealing rings, on the readily accessible valve module can be simply replaced. However, kinematically reversing the setup or fitting sealing points 17, 21 and channel inlets 19, 23 with sealing devices is another conceivable design possibility.

Regardless of the particular embodiment of the invention, the sealing connection can be further enhanced by tube stubs on the channel inlets 19, 23 which, when module 7 is inserted, mate with sealing points 17, 21. In the direction in which the tube stubs are inserted, they may be tapered to make insertion [into] and engagement [with the sealing points] easier, without putting excessive stress on the seals in their horizontal plane just ahead of the end position. Thus, by providing a tapered guide mechanism, it may be possible to reduce an otherwise potentially required horizontal clearance of the seals.

Again regardless of the particular embodiment of the invention, the possibility offered by designing the valves as a valve module is especially useful because it makes it possible allowing the channel inlets to open up into recess 25 in a substantially straight line. In addition to the above described easier access to the channel inlet provided by the recess, an easier access to the channels as such can be ensured. During the required cleaning process with a brush, it is now no longer necessary for the personnel to guide it through extremely curved and therefore difficult-to-access channel inlets and end regions of the channels. The channel inlets run substantially in the direction of the entire longitudinal axis of the channels and can open up in an inclined or vertical manner into the walls of recess 25.

Preferably, they can open up in a slightly inclined manner into the direction of the opening of recess 25 to make it even easier for a cleaning brush to be inserted from the outside.

What is claimed is:

1. An endoscope including:
   (a) an endoscope housing having a module recess formed therein;
   (b) a valve module adapted to be detachably received in the module recess in an operating position, the valve module including at least one flow path, each flow path connected to at least one channel associated with the endoscope when the valve module is in the operating position;
   (c) at least one valve positioned within the valve module for controlling flow through at least one flow path included in the valve module; and
   (d) a sealing connecting point at each end of each flow path in the valve module, each sealing connecting point adapted to form a seal with a different channel inlet of the endoscope housing when the valve module is in the operating position.

2. A The endoscope of claim 1 wherein each valve includes:
   (a) a valve piston detachably positioned in a valve cylinder contained in the valve module.

3. The endoscope of claim 1 wherein the at least one valve comprises a combination air and water valve associated with a water flow channel and an air flow channel in the valve module.

4. The endoscope of claim 1 herein the at least one valve comprises an aspiration valve associated with an aspiration flow channel in the valve module.

5. The endoscope of claim 1 further comprising:
   (a) a combination air and water valve associated with a water flow channel and an air flow channel in the valve module; and
   (b) an aspiration valve associated with an aspiration flow channel in the valve module.

6. The endoscope of claim 1 further comprising:
   (a) a lock structure for locking the valve module in the operating position.

7. A valve module for an endoscope, the valve module comprising:
   (a) a module body comprising a block of material having at least one flow path formed therein;
   (b) at least one valve positioned within the valve module for controlling flow through at least one flow path included in the valve module; and
   (c) a sealing connecting point at each end of each flow path in the valve module, each sealing connecting point adapted to form a seal with a different channel inlet located in a module recess of an endoscope, the module recess adapted to receive the valve module in an operating position.

8. The valve module of claim 7 wherein each valve includes:
   (a) a valve piston detachably positioned in a valve cylinder contained in the valve module.

9. A valve module being adapted to be received in an operating position in a module recess of an endoscope, the valve module comprising:
   (a) a module body comprising a block of material having at least one flow path formed therein;
   (b) at least one valve positioned within the valve module for controlling flow through at least one flow path included in the valve module; and
   (c) a sealing connecting point at an end of one flow path in the module body, the sealing connecting point adapted to form a seal with a particular channel inlet located in the module recess when the module is received in the module recess in an operating position.

* * * * *

UNITED STATES PATENT AND TRADEMARK OFFICE
CERTIFICATE OF CORRECTION

PATENT NO.     : 6,383,132 B1
DATED          : May 7, 2002
INVENTOR(S)    : Viktor Josef Wimmer It is certified that error appears in the above-identified patent and that said Letters Patent is hereby corrected as shown below:

<u>Column 5,</u>
Line 46, change "2. A The" to -- 2. The --

Signed and Sealed this

Thirtieth Day of July, 2002

Attest:

Attesting Officer

JAMES E. ROGAN
*Director of the United States Patent and Trademark Office*